United States Patent [19]

Schoolman

[11] Patent Number: 5,019,828
[45] Date of Patent: May 28, 1991

[54] HIGH RESOLUTION NAVIGATION AND MAPPING SYSTEM

[75] Inventor: Arnold Schoolman, Kansas City, Mo.

[73] Assignee: Schoolman Scientific Corp., Kansas City, Mo.

[21] Appl. No.: 616,746

[22] Filed: Nov. 16, 1990

Related U.S. Application Data

[63] Continuation of Ser. No. 179,656, Apr. 8, 1988, abandoned, which is a continuation-in-part of Ser. No. 935,066, Nov. 21, 1986, Pat. No. 4,737,972, which is a continuation of Ser. No. 671,436, Nov. 14, 1984, abandoned, which is a continuation-in-part of Ser. No. 616,385, Jun. 1, 1984, Pat. No. 4,559,555, which is a continuation-in-part of Ser. No. 351,917, Feb. 24, 1982, abandoned.

[51] Int. Cl.$^5$ .......................... G01S 3/02; G01S 5/02
[52] U.S. Cl. .................................. 342/457; 342/450; 342/451; 342/357
[58] Field of Search ............... 342/352, 356, 351, 450, 342/451, 457, 463–465

[56] References Cited

U.S. PATENT DOCUMENTS

| | | |
|---|---|---|
| 3,059,519 | 10/1962 | Stanton . |
| 3,170,979 | 2/1965 | Baldwin et al. . |
| 3,426,431 | 2/1969 | Anderson . |
| 4,086,632 | 2/1978 | Ingels . |
| 4,312,577 | 1/1982 | Fitzgerald . |
| 4,315,240 | 2/1982 | Spooner . |
| 4,340,878 | 7/1982 | Spooner et al. . |
| 4,360,876 | 11/1982 | Gerault et al. . |
| 4,400,727 | 8/1983 | Aron . |
| 4,400,780 | 8/1983 | Nagao et al. . |
| 4,402,050 | 8/1983 | Tagami et al. . |
| 4,403,291 | 9/1983 | Von Tomkewitsch . |
| 4,427,977 | 1/1984 | Carallo et al. . |
| 4,439,755 | 3/1984 | La Russa . |
| 4,459,667 | 7/1984 | Takeuchi . |
| 4,470,119 | 9/1984 | Haseke et al. . |
| 4,484,192 | 11/1984 | Seitz et al. . |
| 4,502,123 | 2/1985 | Minami et al. . |
| 4,504,913 | 3/1985 | Miura et al. . |
| 4,511,973 | 4/1985 | Miura et al. . |
| 4,513,377 | 4/1985 | Haseke et al. . |
| 4,571,684 | 2/1986 | Takanake et al. . |
| 4,575,722 | 3/1986 | Anderson ............................ 340/705 |
| 4,590,569 | 5/1986 | Rogoff et al. ....................... 364/449 |
| 4,608,656 | 8/1986 | Tanaka et al. . |
| 4,613,864 | 9/1986 | Hofgen ................................. 342/357 |
| 4,630,209 | 12/1986 | Saito et al. . |
| 4,638,438 | 1/1987 | Endo et al. . |
| 4,660,157 | 4/1987 | Beckwith et al. . |
| 4,675,676 | 6/1987 | Takanake et al. . |
| 4,796,190 | 1/1989 | Cummings .......................... 364/449 |
| 4,807,202 | 2/1989 | Cherrie et al. ...................... 367/129 |
| 4,837,700 | 6/1989 | Ando et al. .......................... 342/357 |
| 4,943,861 | 1/1976 | Bull . |

Primary Examiner—Gregory C. Issing
Attorney, Agent, or Firm—Litman, McMahon & Brown

[57] ABSTRACT

A combined navigational and display system for a person including a helmet carrying apparatus for communication, storage and processing of information and for the visual display of information. The navigational system is based on an electromagnetic field generated at sufficiently high frequency preferably by intermediate reference stations. Preferably, the display is part of a flip-up/down visor stereographically showing a local map generated by an information storage device, and the display shows the location of the person on the map as well as the coordinates of that location on the map. The same system can be used by a person in a vehicle for navigational systems using lower carrier frequencies, the antenna and all communication and information storage and processing equipment being mounted on the vehicle and a wireless link being provided between the equipment mounted in the vehicle and the display apparatus mounted in the helmet or the equipment transmits directly to a vehicle mounted display.

4 Claims, 2 Drawing Sheets

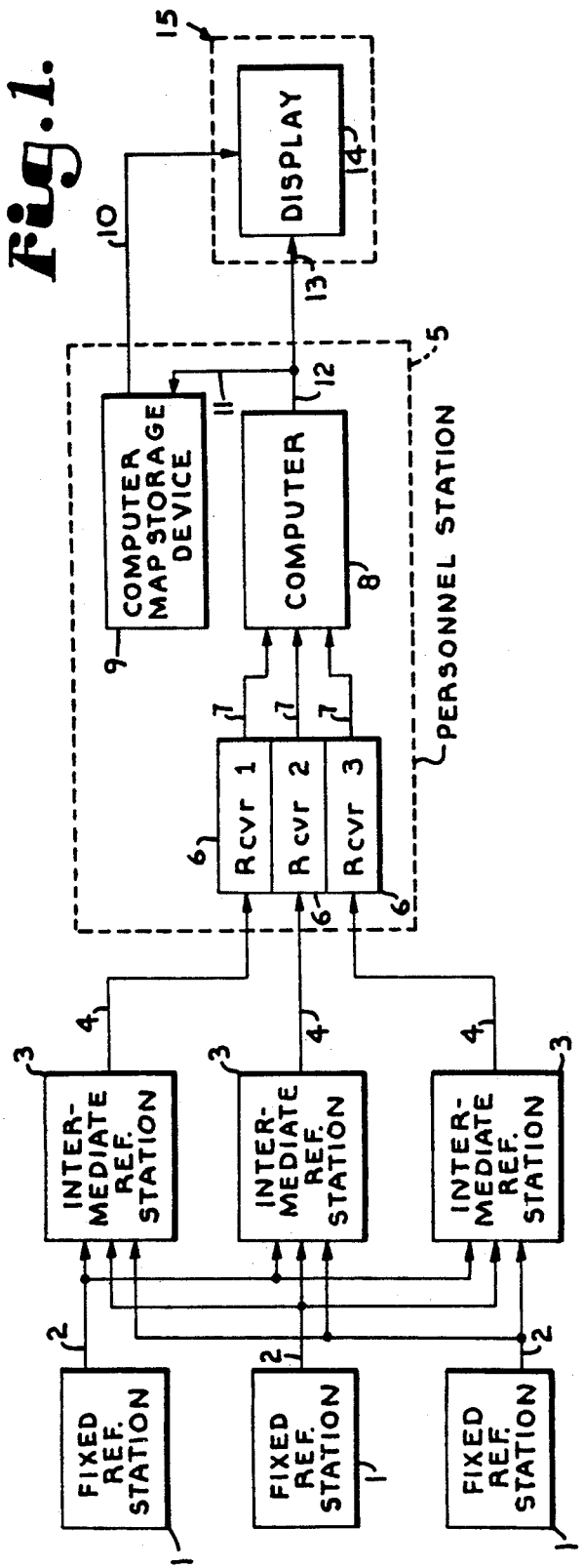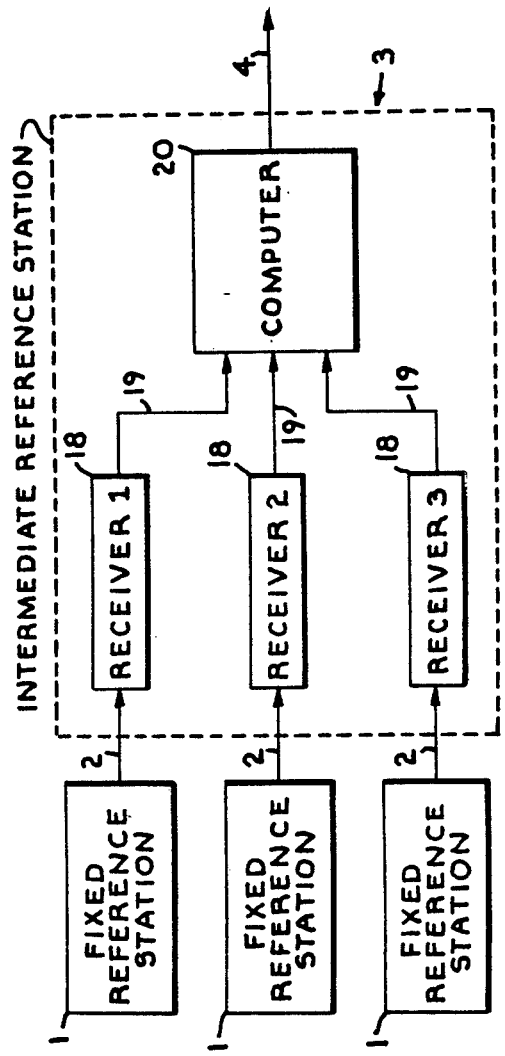

HIGH RESOLUTION NAVIGATION AND MAPPING SYSTEM

CROSS-REFERENCE TO RELATED APPLICATIONS

The present application is a continuation of Ser. No. 179,656 filed Apr. 8, 1988, now abandoned, which was a continuation-in-part, of U.S. Ser. No. 935,066, filed Nov. 21, 1986 on a STEREOSCOPIC FLUROSCOPE ARRANGEMENT, now U.S. Pat. No. 4,737,972; which was a continuation of U.S. patent application Ser. No. 671,436 filed Nov. 14, 1984, abandoned; which was a continuation-in-part of U.S. patent application Ser. No. 616,385 for STEREOSCOPIC REMOTE VIEWING SYSTEM filed June 1, 1984, now U.S. Pat. No. 4,559,555; which was a continuation-in-part of U.S. patent application Ser. No. 351,917 for PORTABLE REMOTE TERMINAL WITH HEAD HELD DISPLAY, filed Feb. 24, 1982, now abandoned, such being incorporated herein by reference.

BACKGROUND OF THE INVENTION

The invention of the present application relates to navigational, information storage/retrieval, and display systems and, in particular, to the determination by an individual of his or her location relative to a surrounding region and positioning of such location on a visual map.

In todays world, it is becoming increasingly important to know ones position relative to the earth with relative precision. For example, the soldier needs to know where he or she is and where the enemy is, the delivery person trying to find a customer in a unfamiliar region needs to know his or her location relative to the point of delivery, travelers need to know their location, ships at sea need to be precisely located, etc. Todays technology is providing the means to pinpoint ones location on earth with some degree of accuracy. For example, the U.S. government's satellite Navstar system (when complete) will allow quite precise positioning of ships carrying the means to use such a system. Likewise, the aviation Loran-C guidance system is utilized to provide aircraft with a reasonably accurate positioning of the aircraft relative to the earth beneath it.

However, guidance, positioning or mapping systems for individuals (and also usually for land vehicles) have been rather unsophisticated, relying on methods that measure distance and direction to determine position. In such methods, errors become magnified.

In addition, it is desirable to have a mapping system that can display to a user his or her position relative to surrounding terrain or city environment, that preferably will provide the user with a stereoscopic view of the surrounding terrain relative to the viewer's position and that may be carried in a self-contained unit by an individual, preferably in a head mountable helmet.

SUMMARY OF THE INVENTION

Information concerning the location of remote signal transmitters and receiving means for receiving signals from remote, relatively stationary remote signal transmitters (such as the Navstar or Loran-C transmitters) is contained in the transmissions of such transmitters and/or in the receiving means of an apparatus contained within a helmet worn by a user or within an apparatus carried by a vehicle transporting the user. If the apparatus is carried by a vehicle, the user's helmet preferably is self-contained and includes a display device. The helmet preferably receives a signal indicating the user's location from the vehicle's equipment by a wireless link between the vehicle and the user's helmet. In this manner, the user may be somewhat remote from the vehicle or may alternately view a map produced by the apparatus on a display device associated with the vehicle. Preferably, the display apparatus is located in or connected to the helmet and displays both a local map generated by the processing of stored information and also the location of the user relative to the local map by a point on the map as well as by the coordinates of that point on the map.

Whether the apparatus is totally in the helmet or only the display is in the helmet typically depends on the carrier frequencies of the electromagnetic fixed navigational system being utilized. Lower frequencies require larger antennas, and, therefore, for some transmitters, at least the antenna is mounted on the vehicle carrying the user. Higher frequencies permit the antenna and all the other apparatus to be mounted on and in the helmet.

Preferably, the apparatus of the present invention receives an electromagnetic navigational signal from a reference signal transmission system that transmits from at least three fixed reference stations (e.g., earth-fixed, such as Loran-C, or fixed-orbit satellites, such as Navstar). Such signals are in the form of electromagnetic radiation. Also preferably, several portable and/or transportable intermediate reference stations operably functioning as relay stations convert any low frequency of the fixed stations to a higher carrier frequency so that navigational information can be received by a receiver located in a self-contained user's helmet using a stub antenna mounted on the helmet. Such relay stations include mechanisms to effectively locate themselves with reference to the fixed stations, and then transmit their locations using higher carrier frequencies directly to the helmet.

A special-purpose digital computer at each relay station exercises a governing equation to convert the information received from the fixed stations to the earth coordinates of the location of each of the relay stations. Similarly, a special-purpose digital computer at the helmet exercises another equation to convert the information received from the relay stations to the earth coordinates of the helmet. Further, mathematical operations by the computer convert these coordinates into map coordinates for display with a map of the region surrounding the user. Such conversion takes place after an appropriate map stored in a computer map storage device associated with the computer is retrieved and displayed, the map being selected based on the coordinates. The helmet computer is then able to convert the map coordinates into display coordinates and display by a mark the actual location of the user on the map.

Also preferably, the display device is mounted in a flip-up/down visor attached to the helmet, and includes two displays (one for each eye) stereoscopically synchronized with each other so as to effect a three-dimensional image of the surrounding terrain to the viewer. The viser may also be of the "look past" type that allows the viewer to see both the image on the viser and the surrounding terrain simultaneously to allow comparison.

Alternatively, the transmissions from the fixed stations may be received by a single intermediate reference station mounted on a vehicle which includes a computer to determine the location of the vehicle by means similar to that used in the multiple-relay-station system. The information for the display device carried by the user is then transmitted by wireless link to the individual wearing the helmet who is either on, in or nearby the vehicle so that the display device in the flip-up/down visor can show the location of the relay station relative to the map coordinates.

OBJECTS OF THE INVENTION

Therefore, the objects of the present invention are: to provide a mapping system receiving and converting reference signals from fixed reference stations, an apparatus to convert such signals to a specific location of one or more relocatable (portable or transportable) intermediate reference (relay) stations or a personnel station mounted in a user's helmet; to provide such an apparatus including mechanism to visually display the location thus obtained by a mark on the image of the map; to provide such an apparatus wherein the image is a stereographic image of the surrounding environment; to provide such an apparatus including a display device mounted in the flip-up/down visor of a helmet; to provide such an apparatus that is easy to use, relatively simple to manufacture and particularly well adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a block diagram of a system according to the invention including fixed stations, wireless links, relay stations and wireless links to receivers in a display station.

FIG. 2 is a block diagram of an intermediate reference (relay) station.

DETAILED DESCRIPTION OF THE INVENTION

Figure 3:
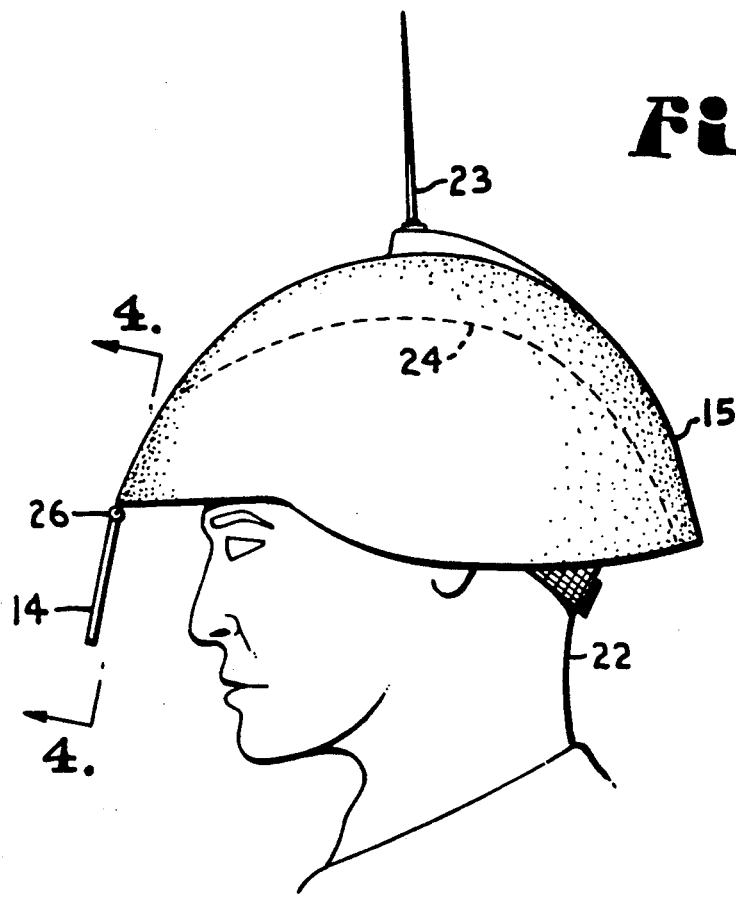
FIG. 3 is a side elevational view of a helmet worn by a user, and containing antenna and a receiver/computer connecting to a display mounted on a flip-up/down visor of the helmet.
Figure 4:
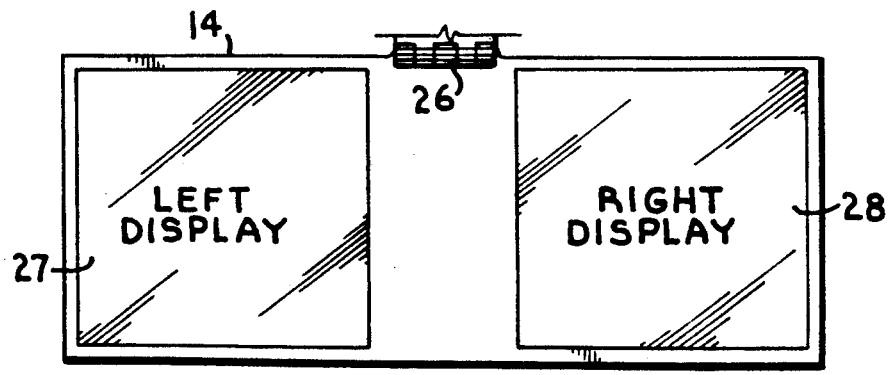
FIG. 4 is a fragmentary and enlarged cross-sectional view of the helmet, taken along line 4—4 of FIG. 3.

As required, detailed embodiments of the present invention are disclosed herein; however, it is to be understood that the disclosed embodiments are merely exemplary of the invention, which may be embodied in various forms. Therefore, specific structural and functional details disclosed herein are not to be S interpreted as limiting, but merely as a basis for the claims and as a representative basis for teaching one skilled in the art to variously employ the present invention in virtually any appropriately detailed structure.

Referring to the drawings in the disclosed embodiment of the present invention:

In FIG. 1, three "fixed" position stations 1 (that may be earth stations at fixed locations, or three satellite stations in fixed orbits), transmit an electromagnetic signal. Each of the three stations broadcasts at a different carrier frequency over wireless links 2 to each of three relay stations 3. The carrier frequency identifies the station 1 to the relay stations 3, and each relay station 3 includes the capacity, to calculate the location at any time of each station 3 based upon the signal from each station 1 and a suitable algorithm performed by a computer associated with each relay station 3. Thus, each relay station 3 contains three receivers each receiving each transmission of each fixed station 1. The difference in the distances of each station 3 from two of the stations 1 can be determined by methods well known in the art, thereby locating station 3 on one member of a family of hyperbolic curves with foci at the locations of those two stations 1. Similarly, one of the two stations 1, together with the third station 1, enable each relay station 3 to locate itself on a member of another family of hyperbolic curves with foci at the two pertinent stations 1. The intersection of the two hyperbolic curves is the location of the specific relay station with reference to the fixed locations of the fixed stations 1. Each relay station 3 then calculates the coordinates of the relay station location.

The three relay stations 3 then act as the intermediate reference stations for a user or personnel station 5 by broadcasting over respective wireless links 4 to receivers 6 in personnel station 5. Since the relay stations 3 are portable and/or transportable, each relay station 3 transmits information containing its location that has been previously determined relative to the fixed stations 1. With this information and a unique identifying carrier frequency identifying each relay station 3, a special-purpose computer 8 receiving the information over a communication links 7 is able to compute the location of the personnel station 5 with reference to the relay stations 3 and hence with reference to the fixed stations 1.

Associated with the computer 8 is a map information storage device 9 which contains information to generate a graphical display of a map for the vicinity surrounding the location calculated by the computer 8 as the location of the personnel station 5. The retrieval of this information is triggered by output 12 of the computer 8 that becomes input 11 of the computer map storage device 9, and also input 13 of a visual display device 14. An output 10 of the map storage device 9 transfers the map to the display device 14. Superimposed on the map shown on the display device 14 is an identifying mark provided by input 13 and showing the location of the station 5 on the map. If personnel station 5 is mounted separately on a vehicle, then a helmet 15 is provided that receives information by wireless link (10 and 13) from the personnel station 5. Preferably, the personnel station 5 and display device 14 are located in the helmet 15.

In FIG. 2, a relay station 3 is shown that operably functions to locate itself with reference to the fixed stations 1. Each relay station 3 includes three receivers 18 to receive an identifying transmission by wireless link 2 from the fixed stations 1. Outputs 19 of the receivers 18 are combined by a computer 20 to determine the location of the relay station 3. The wireless links 4 carry the transmission from each relay station 3, at an identifying unique carrier frequency, and contain information on the location of the relay station 3 with reference to stations 1 so that the personnel station 5 can use these three transmissions to locate itself.

In FIG. 3, the helmet 15 is worn by a user 22 and contains communications and computer equipment 24 and stub antenna 23. Electrical power for the equipment 24 may be self-contained batteries or batteries carried by the user, as, for example, in a belt pack. The stub antenna 23 is used at adequately high carrier frequencies from the relay stations 3 (or alternatively from the fixed station 1, if such provide a suitably high frequency). The relay stations 3 may be located in vehicles or may be stand alone units. If a relay station 3 is located in the vehicle in which the individual is riding, then only that one relay station 3 is used and the location of that specific relay station 3 is transmitted by high frequency wireless link to the helmet 15 to be connected into a location on a map and visualized on the display device 14.

The display device 14 is connected to the communication and computer equipment 24 by suitable electric connectors and to the remainder of the helmet 15 by a hinge 26 to allow the display device 15 to be rotated upwardly out of the visual path when not in use. The display device 14 includes left display 27 and right display 28 which preferably each optically show images that are about 8° to 10° separated at the source thereof so as to produce a stereoscopic composite image to a viewer 22. That is the map storage device 9 stores a pair of maps for each section of a grid and each map of each pair is constructed at a slight viewing angle relative to the other map of each pair.

Even though the present invention has been shown and described with reference to particular embodiments, various changes and modifications which are obvious to a person skilled in the art, and to which the invention pertains, are deemed to lie within the scope of the invention. Furthermore, details of communications design and the design of the logic circuits to embody the special-purpose computers are well known to persons skilled in the art and have, therefore, been omitted for the sake of clarity.

What is claimed and desired to be secured by Letters Patent is as follows:

1. A portable navigation system for locating a mobile personnel station operating within a predetermined region, said location being relative to a set of relatively distant, substantially fixed reference stations broadcasting respective location signals and comprising:
   (a) a plurality of portable relay stations;
   (b) each relay station, when inactive, being adapted to be transported to a location which is relatively near the personnel station operating region, each said relay station including relay receiver means which, upon activation of said relay station, receives location signals from said reference stations, each said relay station also including relay computer means deriving current location coordinates of said relay station from said location signals and wireless link means to output a respective relay station location signal indicating an absolute location of said relay station; and
   (c) said mobile personnel station including:
      (1) personnel receiver means receiving the relay location signals from said plurality of relay stations;
      (2) map storage means storing data representing a plurality of stereoscopic maps of the region of operation;
      (3) display means operable to stereoscopically display said maps and station indicia representing a relative location of said personnel stations on a map displayed on said display means; and
      (4) personnel computer means interfaced among said personnel receiver means, said map storage means, and said display means; said personnel computer means calculating absolute personnel station coordinates of a location of said personnel station relative to said relay stations, causing a map surrounding said location of said personnel station to be retrieved from said map storage means and displayed on said display means, and causing said station indicia to be displayed on the displayed map at a position corresponding to said personnel station coordinates.

2. A system as set forth in claim 1 and including:
   (a) said receiver means, said map storage means, said display means, and said computer means being mounted in a helmet adapted to be worn by an individual.

3. A system as set forth in claim 1 including:
   (a) said distant reference stations are fixed orbit satellite stations.

4. A system as set forth in claim 1 wherein:
   (a) said distant reference stations are Loran C stations.

* * * * *